United States Patent [19]
Drezdzon et al.

[11] Patent Number: 5,157,184
[45] Date of Patent: Oct. 20, 1992

[54] CATALYST AND PROCESS FOR OXIDATIVELY DEHYDROGENATING A LOWER-ALKYL-SUBSTITUTED ETHYLBENZENE

[75] Inventors: Mark A. Drezdzon, Aurora; Eric J. Moore, Carol Stream; Marc L. Kullberg, Lisle, all of Ill.

[73] Assignee: Amoco Corporation, Chicago, Ill.

[21] Appl. No.: 399,308

[22] Filed: Aug. 28, 1989

Related U.S. Application Data

[63] Continuation-in-part of Ser. No. 194,108, May 16, 1988, abandoned.

[51] Int. Cl.$^5$ .............................................. C07C 5/333
[52] U.S. Cl. .................................... 585/444; 585/440; 585/443
[58] Field of Search ..................... 585/443, 444, 440

[56] References Cited

U.S. PATENT DOCUMENTS 3,766,191 10/1973 Cichowski et al. .................. 585/443
3,957,897 5/1976 Vrieland et al. .................... 585/443

Primary Examiner—Asok Pal
Attorney, Agent, or Firm—Reed F. Riley; William H. Magidson; Robert J. Wagner

[57] ABSTRACT

Catalyzed vapor-phase processes are taught for the oxidative dehydrogenation of a lower-alkyl-monosubstituted ethylbenzene to a lower-alkyl-monosubstituted styrene. Barium pyrophosphate and the pyrophosphate-containing calcination product of $KFe_3H_{14}(PO_4)_8 \cdot nH_2O$, n running between about 1 to about 4, are shown to effectively catalyze these dehydrogenations at a low enough temperature such that very little cracking of the lower alkyl group occurs which gives superior conversions and selectivities to the corresponding styrenes and lengthened catalyst lifetime. An improved method of preparation of $KFe_3H_{14}(PO_4) \cdot nH_2O$ is described as well as the new material which is essentially $KFe_3H_6(P_2O_7)_4$.

6 Claims, No Drawings

CATALYST AND PROCESS FOR OXIDATIVELY DEHYDROGENATING A LOWER-ALKYL-SUBSTITUTED ETHYLBENZENE

RELATED APPLICATIONS

This application is a CIP of U.S. Ser. No. 194,108 filed May 16, 1988, now abandoned.

BACKGROUND OF THE INVENTION

This invention relates to the catalytic dehydrogenation of a lower-alkyl-substituted ethylbenzene, and, more particularly, to the oxidative dehydrogenation of a $C_1$ to $C_4$ alkyl-monosubstituted ethylbenzene over an inorganic, pyrophosphate-containing catalyst to form a $C_1$ to $C_4$ alkyl-monosubstituted styrene.

The dehydrogenation of an organic compound such as an alkane or alkyl-substituted aromatic is an important industrial process and, although the reaction occurs thermally, it is more often run catalytically, most often in the absence of oxygen in a vapor-phase reaction. An example of such a nonoxidative reaction is the conventional synthesis of styrene which involves the dehydrogenation of ethylbenzene in the absence of oxygen over potassium-and/or chromia-promoted iron oxide catalysts at about 570°–640° C. Other examples of such nonoxidative, catalytic dehydrogenations are the reaction of p-ethyltoluene to p-methylstyrene at 625° C. over a copper aluminum borate as taught in U.S. Pat. No. 4,590,324, and the reaction of an alkylaromatic containing at least two carbon atoms in at least one alkyl group to form an alkenyl aromatic over an aluminum borate doped with an alkali or alkaline earth compound as taught in U.S. Pat. No. 4,645,753. In the temperature range employed, there is, in the non-oxidative dehydrogenation, a significant amount of catalyst coking, hydrocarbon cracking and a less than desirable catalyst lifetime and selectivity. This is true particularly when the ethylbenzene is alkyl-substituted, for example, in the dehydrogenation of an ethyl toluene to a methylstyrene and becomes more severe with increase in the size of the alkyl substituent.

If an oxidant such as air or diluted oxygen is added to the catalytic dehydrogenation of ethylbenzene to make the reaction oxidative, the process temperature range can be reduced to the 450°–550° C. range resulting in less melting and catalyst coking. In U.S. Pat. No. 3,957,897, the use of certain alkali metal pyrophosphates is taught for the oxidative dehydrogenation of ethylbenzene to styrene in the temperature range 450°–650° C. The magnesium salt is taught as being most effective of the magnesium, calcium, and strontium for the process, and the barium salt, which is described only for comparative purposes, is taught as having a very low conversion (28.5%) and an average selectivity (92.6%).

The compound $K_3Fe_3H_{14}(PO_4)_8 \cdot 4H_2O$ is described in the open literature in J. Agr. Food Chem. 14, (1) 27–33 (1966) and it is there reported that it may be synthesized from a soluble source of Fe (III) such as $FeCl_3 \cdot 6H_2O$. The calcination of this material has not been reported nor has the calcination product, $KFe_3H_6(P_2O_7)_4$.

Now it has been found that barium pyrophosphate is, contrary to the '897 patent teaching, more effective than other alkaline earth pyrophosphates when used in catalysts for the oxidative dehydrogenation of p-(t-butyl)ethylbenzene to p-(t-butyl)styrene, and can lead to conversions in excess of 42 weight percent, the catalyst exhibiting substantial resistance to deactivation and coking. Excellent conversion and selectivity in the dehydrogenation of a lower alkyl-monosubstituted ethylbenzene have also been found for the pyrophosphate-containing calcination product of $K_3Fe_3H_{14}(PO_4)_8 \cdot nH_2O$ for which an improved method of preparation has been found.

BRIEF DESCRIPTION OF THE INVENTION

In one aspect, the invention describes a vapor-phase process comprising contacting under dehydrogenation conditions a lower-alkyl-monosubstituted ethylbenzene and an oxygen-containing gas containing less than about twenty mol percent oxygen with a catalyst composition containing the pyrophosphate calcination product of the compound $KFe_3H_{14}(PO_4)_8 \cdot nH_2O$, wherein n is about four or less, to selectively form a lower-alkyl-monosubstituted styrene.

In another aspect, the invention embraces making the compound $KFe_3H_{14}(PO_4)_8 \cdot nH_2O$ wherein n runs between about 1 and about 4 by contacting $Fe_2O_3$ with a solution made from phosphoric acid and a potassium carbonate to form a slurry, heating and agitating said slurry for an extended period, and isolating said $KFe_3H_{14}(PO_4)_8 \cdot nH_2O$.

In still another aspect, the invention describes a new material essentially of formula $KFe_3H_6(P_2O_7)_4$ which can be made by calcination of $K_3Fe_3H_{14}(PO_4)_8 \cdot nH_2O$ where n runs between about 1 and about 4, at a temperature above about 400° C. By "essentially of formula $KFe_3H_6(P_2O_7)_4$" it is meant that small amounts of impurities may be present in combination with the pyrophosphate.

In yet another aspect, the invention encompasses a vapor-phase process comprising contacting under dehydrogenation conditions p-(t-butyl)ethylbenzene and an oxygen-containing gas containing less than about twenty mol percent oxygen with a catalyst composition containing barium pyrophosphate to selectively form a lower-alkyl-monosubstituted styrene.

DETAILED DESCRIPTION OF THE INVENTION

Organic compounds which may be dehydrogenated by this invention include lower-alkyl-monosubstituted ethylbenzenes. By lower-alkyl is meant a $C_1$ to $C_5$ alkyl group. More preferred is the use of $C_1$ to $C_4$ alkyl-monosubstituted ethylbenzene, and most preferred is the use of a t-butylethylbenzene, particularly para-t-(butyl)ethylbenzene.

The barium pyrophosphate catalyst of this invention can be prepared by calcining the corresponding barium monohydrogen phosphate in accordance with the following:

It is preferred to carry out the calcination between about 500° and about 650° C. Too high or too low a calcination temperature can be detrimental to the catalytic properties of the solid as is well-known to those skilled in the art.

Another route for preparing the barium pyrophosphate is to heat the alkaline earth monoammonium phosphate eliminating $H_2O$ and $NH_3$. This process is characterized by the following equation:

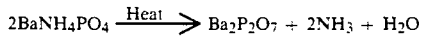

The preferred calcination temperature range is about the same as above.

A third procedure for preparing the barium-containing catalyst is to react a water soluble barium salt with $NH_4H_2PO_4$, $(NH_4)_2HPO_4$ or $H_3PO_4$. The amount of the mono or diammonium phosphate or phosphoric acid should be in excess of that needed to form the orthophosphate and at least sufficient to form the pyrophosphate. The precipitate which forms in the reaction is filtered, dried and calcined. In this procedure the $PO_4^{3-}$/barium ratio should preferably be less than 2. Calcination is preferably done above about 500° C. until the material loses no further water, however, too high a calcination temperature can be detrimental as can be understood by one skilled in the art.

The $KFe_3H_{14}(PO_4)_8 \cdot 4H_2O$ precursor to the potassium iron pyrophosphate material can be made by the method found in J. Agr. Food Chem. 14, (1) 27-33 (1966). After drying the material it is calcined at about 400° to about 650° C., more preferably at about 450° to about 550° C., until further weight loss is minimal. Calcination produces a substance which is essentially the compound $KFe_3H_6(P_2O_7)_4$. Again, too high or too low a calcination temperature can be detrimental as can be understood by one skilled in the art. The barium pyrophosphate and pyrophosphate calcination product of $KFe_3H_{14}(PO_4)_8 \cdot 4H_2O$ can be used neat or supported on a material such as silica, alumina, silica-alumina or magnesia. Preferably, they are used without a support.

An improved preparation of the above compound which avoids the production of a large amount of hydrogen chloride involves using $Fe_2O_3$ as the iron source. Conveniently, the $Fe_2O_3$ can be slurried with an aqueous solution made from phosphoric acid, preferably concentrated phosphoric acid, a potassium carbonate such as $K_2CO_3$ or $KHCO_3$, heating the slurry for up to about five or six days at a temperature between about 80° to about 120° C., preferably about 90° to 110° C., for up to about 5 or 6 days. The $KFe_3H_{14}(PO_4)_8 \cdot 4H_2O$ can then be isolated as a solid by filtration and washed and dried.

In the inventive process, the molar ratio of oxygen to alkyl aromatic compound fed into the dehydrogenation reactor can range from about 0.5 to about 4.0 mols of oxygen per mol of aromatic hydrocarbon, but a preferred range is from about 0.5 to about 2.5 mols. Most preferred is the use of about 1.1 to about 1.4 mols oxygen per mol of aromatic compound.

The oxygen can be pure oxygen, but it is preferred to use oxygen diluted with an inert diluent such as nitrogen. Most commonly, air is used as the oxygen source and further diluted with an inert gas if desired. Diluents when used can be one of the rare gases, nitrogen, carbon dioxide or steam and the like.

The space velocity (wt/wt/hr) used in the dehydrogenation reaction can range from about 0.01 to about 10, but a preferred range is from about 0.1 to about 5. Most preferred is the use of a range from about 0.1 to about 1 $hr^{-1}$. The pressure at which the reaction can be run is in the range from about 0.5 psi to about 300 psi, but it is preferable to operate in the pressure range of about 15 to about 100 psi for optimal results. The oxidative dehydrogenation reaction can be effected in a temperature range from about 300° to about 700° C., but a preferred range is from about 450° to about 600° C. Care should be exercised to avoid explosive mixtures when feeding the alkyl aromatic compound and oxygen into the reactor as can be understood by one skilled in the art. Generally, the dehydrogenation reaction produces only small amounts of by-products which can be separated by conventional means. When p-(t-butyl)ethylbenzene is used, small amounts of isopropenylstyrene and isobutenylstyrene form. The isopropenylstyrene can be separated from the desired product by active carbon adsorption.

The following Examples will serve to illustrate certain embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

In each of the dehydrogenation Examples below a 25 ml charge of catalyst pellets was loaded in a 0.75 in stainless steel tubular reactor and the body temperature of the reactor was raised to 500° C. in a single-zone furnace. The gas flow was 7% by volume oxygen in nitrogen used at a total flow rate of 55 ml/min. The molar diluent ratio:nitrogen/t-butylethylbenzene was 18.4 and the liquid t-butylethylbenzene flow was 0.024 ml/min. The weight hourly space velocity was 0.04/$hr^{-1}$. Liquid products were determined quantitatively by gas chromatography to give selectivities and conversions so that the yields and selectivities are based upon conversion to liquid products. When total conversions (to gaseous products as well) are calculated they are about 4% higher and selectivities to the alkylstyrene are about 8% lower. All percentages are in weight percent.

EXAMPLE 1

A 151.4 g portion of barium nitrate was added to 2000 ml of distilled $H_2O$ and the pH adjusted to 6.3 using $NH_4OH$. A solution of ammonium hydrogen phosphate dibasic (89.3 g in 500 ml distilled $H_2O$) was prepared and the pH adjusted to 7.2 using $HNO_3$. The barium nitrate solution was added to the ammonium hydrogen phosphate solution dropwise with vigorous stirring. The pH was kept monitored and kept in the range 5.5 to 6.5. The final pH was 6.1. The precipitate which formed over the course of addition was filtered and rinsed with distilled $H_2O$. The resulting white solid was vacuum dried at 125° C. for 16 hr. The dried powder (69.2 g) was combined with 1.8 g of Sterotex (2.53%) and then pelletized into ⅛ in diameter pellets. The pellets were calcined at 550° C. for 8 hr and used as the barium pyrophosphate catalyst below.

EXAMPLE 2

Magnesium, calcium and strontium pyrophosphates were made in pellet form by the procedure of Example 1 and used as catalysts as below in Example 7.

EXAMPLE 3

Preparation of $KFe_3H_6(P_2O_7)_4$ was as follows. A 2 l beaker was charged with 1001 g of 85% phosphoric acid. While stirring the phosphoric acid with an overhead mechanical stirrer, a 233.3 g portion of powdered FeCl$_3$.6H$_2$O was slowly added followed by a 23.33 g portion of KCl. After stirring the mixture for about 20 min, the mixture was filtered through a coarse glass frit to remove any insoluble material. The filtrate was then transferred to a 1 l beaker and covered with a watch glass. After standing for 4 days, the precipitate which had collected along the walls of the beaker was scraped off and the entire mixture manually stirred. After standing an additional day, the mixture was filtered on a coarse glass frit. The filter cake was reslurried with 350 ml methanol and filtered, a washing technique which was repeated 3 times. The light pink solid was then dried in a vacuum oven overnight at 300° F., affording a 192.3 g quantity of KFe$_3$H$_{14}$(PO$_4$)$_8$.4H$_2$O.

Approximately ⅔ of the dried material was ground and sieved to 8/12 mesh size. Total weight of 8/12 mesh size KFe$_3$H$_{14}$(PO$_4$)$_8$.4H$_2$O equaled 123.94 g. This material was calcined at 500° C. for 12 hr resulting in a weight loss of 15.46 g or 12.47% (theoretical weight loss corresponding to conversion to KFe$_3$H$_6$(P$_2$O$_7$)$_4$ is 13.69%). Analysis showed Fe, 18.0% (18.44%); K, 4.7% (4.30%); P, 25.2% (27.28%). Theoretical values for the formula KFe$_3$H$_6$(P$_2$O$_7$)$_4$ are in the parentheses.

EXAMPLE 4

The solid product of Example 3 was calcined at 500° C. for 12 hr, crushed, and sieved to 8/12 mesh size.

EXAMPLE 5

The solid product of Example 3 was calcined at 800° C. for 12 hr, crushed, and sieved to 8/12 mesh size.

EXAMPLE 6

The catalyst of Example 1 was used to oxidatively dehydrogenate p-(t-butyl)ethylbenzene to p-(t-butyl)styrene. The results are shown below in Table 1.

TABLE 1

% Selectivity and Conversion in the Oxidative Dehydrogenation of p-(t-butyl)ethylbenzene

| On Stream Time (hr) | % Conversion | % Selectivity** |
|---|---|---|
| 16 | 56 | 97 |
| 21 | 55 | 97 |
| 37 | 55 | 97 |
| 45 | 56 | 96 |
| 61 | 56 | 97 |
| 81 | 56 | 97 |
| 105 | 55 | 98 |
| 115 | 56 | 98 |
| 131* | 42 | 98 |

*Space velocity was changed by a factor of 2.5.
**Major dialkenylbenzene product impurities are isopropenylstyrene (about 0.045%) and isobutenylstyrene (about 0.085%).

COMPARATIVE EXAMPLE 7

Various alkaline earth pyrophosphates were used to oxidatively dehydrogenate p-(t-butyl)ethylbenzene to p-(t-butyl)styrene. The results are shown below in Table 2.

TABLE 2

Comparison of % p-(t-butyl)ethylbenzene Conversions and p-(t-butyl)styrene Selectivities for Several Alkaline Earth Pyrophosphate Catalysts

| Catalyst* | On Stream Time (hr) | % Conversion | % Selectivity |
|---|---|---|---|
| Mg$_2$P$_2$O$_7$ | 89 | 47 | 94 |
| Ca$_2$P$_2$O$_7$ | 91 | 43 | 95 |
| Sr$_2$P$_2$O$_7$ | 93 | 51 | 96 |
| Ba$_2$P$_2$O$_7$ | 105 | 55 | 98 |

*Catalysts used were made according to Examples 1 and 2.

EXAMPLE 8

The catalyst of Example 3 was used to oxidatively dehydrogenate p-(t-butyl)ethylbenzene to p-(t-butyl)styrene. The results are shown below in Table 3.

TABLE 3

% Selectivity and Conversion in the Oxidative Dehydrogenation of p-(t-butyl)ethylbenzene

| On Stream Time* (hr) | % Conversion | % Selectivity** |
|---|---|---|
| 5 | 56 | 97 |
| 23 | 52 | 98 |
| 29 | 50 | 97 |
| 47 | 50 | 97 |
| 53 | 50 | 97 |
| 70 | 50 | 97 |
| 77 | 52 | 97 |
| 95 | 52 | 91 |
| 101 | 62*** | 68 |
| 122 | 46 | 96 |
| 144 | 53 | 97 |
| 167 | 52 | 97 |
| 173 | 52 | 97 |
| 192 | 42*** | 97 |
| 196 | 45 | 97 |

*WHSV for this catalytic run was 0.077 hr$^{-1}$.
**% isopropenylstyrene (IPS) and % isobutenylstyrene (IBS) impurities in the product were about the same as in Example 5.
***Variation due to temperature fluctuations during the run.

EXAMPLE 9

The catalyst of Example 4 was used to oxidatively dehydrogenate p-(t-butyl)ethylbenzene to p-(t-butyl)styrene. The results are shown below in Table 4.

TABLE 4

% Selectivity and Conversion in the Oxidative Dehydrogenation of p-(t-butyl)ethylbenzene

| On Stream Time* (hr) | % Conversion | % Selectivity |
|---|---|---|
| 18 | 49 | 97 |
| 23 | 49 | 96 |
| 42 | 48 | 97 |
| 48 | 49 | 97 |
| 66 | 49 | 96 |
| 71 | 49 | 96 |
| 93 | 49 | 96 |
| 117 | 47 | 96 |
| 138 | 47 | 96 |
| 144 | 49 | 96 |
| 163 | 49 | 95 |

*WHSV for this catalytic run was 0.077 hr$^{-1}$.

EXAMPLE 10

The catalyst of Example 5 was used to oxidatively dehydrogenate p-(t-butyl)ethylbenzene to p-(t-butyl)styrene. The results are shown in Table 5.

TABLE 5

% Selectivity and Conversion in the
Oxidative Dehydrogenation of p-(t-butyl)ethylbenzene

| On Stream Time (hr) | % Conversion | % Selectivity |
|---|---|---|
| 6 | 37 | 35 |
| 22 | 13 | 95 |
| 30 | 22 | 91 |

EXAMPLE 11

A 2 l, 3-neck round-bottomed flask equipped with a reflux condenser, thermometer, mechanical stirrer, and electric heating mantle was charged with 1472 g of 85% phosphoric acid, 100.7 g of $Fe_2O_3$, and 31.4 g of $K_2CO_3$. The mixture was heated at 97°–99° C. with stirring for 5 days. After cooling, the mixture was filtered and the product washed and dried as described in Example 3, affording 365 g of $KFe_3H_{14}(PO_4)_8 \cdot 4H_2O$ (82.5% yield based on the amount of iron used). The product was analyzed and the following results were obtained:

Calculated for $KFe_3H_{14}(PO_4)_8 \cdot 4H_2O$ (K, 3.7%; Fe, 15.9%; P, 23.5%). Found (K, 3.3%; Fe, 15.5%; P, 22.8%). The surface area of the product using the BET procedure employing nitrogen was less than 5 $m^2/g$. Scanning electron microscopy revealed a homogeneous matrix of well-formed, distorted hexagonal block crystals.

A 306.5 g sample of $KFe_3H_{14}(PO_4)_8 \cdot 4H_2O$ as made above (8/12 mesh particles) was calcined in air at 500° C. for 12 hr yielding 268.4 g of light tan $KFe_3H_6(P_2O_7)_4$. The product was analyzed and the following results were obtained:

Calculated for $KFe_3H_6(P_2O_7)_4$ (K, 4.3%; Fe, 18.4%; P, 27.3%). Found K, 4.3%; Fe, 18.4%; P, 27.6%). Calculated weight loss was 13.7% versus an observed weight loss of 12.4%. The surface area of the product using the BET procedure employing nitrogen was less than 5 $m^2/g$. Scanning electron microscopy revealed a homogeneous matrix of fragmented, irregular platelike crystals.

EXAMPLE 12

The pyrophosphate of Example 11 was used to oxidatively dehydrogenate p-(t-butyl)ethylbenzene to p-(tbutyl)styrene. The results are shown below in Table 6.

TABLE 6

| On Stream Time (hr) | % Conversion | % Selectivity |
|---|---|---|
| 4 | 37 | 97 |
| 23 | 37 | 97 |
| 45 | 35 | 97 |
| 77 | 35 | 97 |
| 115 | 34 | 97 |

What is claimed is:

1. A vapor-phase process comprising contacting under dehydrogenation conditions a lower-alkyl-monosubstituted ethylbenzene and an oxygen-containing gas containing less than about 20 mol percent oxygen with a catalyst composition containing the pyrophosphate-containing calcination product of the compound $KFe_3H_{14}(PO_4)_8 \cdot nH_2O$, wherein n is about 4 or less, to selectively form a lower-alkyl-monosubstituted styrene.

2. The process of claim 1 wherein said oxygen-containing gas contains less than about 10 mol percent oxygen.

3. The process of claim 2 wherein said lower-alkyl-monosubstituted ethylbenzene and styrene are each $C_1$ to $C_4$ lower-alkyl-monosubstituted.

4. The process of claim 3 wherein said organic compound is a $C_1$ to $C_4$ lower-alkyl-monosubstituted ethylbenzene.

5. The process of claim 4 wherein said organic compound is a t-butylethylbenzene.

6. The process of claim 4 wherein said organic compound is para-(t-butyl)ethylbenzene.

* * * * *